United States Patent
Adamy et al.

(10) Patent No.: US 10,849,929 B2
(45) Date of Patent: Dec. 1, 2020

(54) COMPOSITION AND METHOD FOR ALLERGEN DEACTIVATION

(71) Applicant: Church & Dwight Co., Inc., Princeton, NJ (US)

(72) Inventors: Steven T. Adamy, Lawrenceville, NJ (US); Timothy C. Morris, Morton, PA (US)

(73) Assignee: Chuch & Dwight Co., Inc., Princeton, NJ (US)

( * ) Notice: Subject to any disclaimer, the term of this patent is extended or adjusted under 35 U.S.C. 154(b) by 29 days.

(21) Appl. No.: 15/691,234

(22) Filed: Aug. 30, 2017

(65) Prior Publication Data

US 2018/0055880 A1 Mar. 1, 2018

Related U.S. Application Data

(60) Provisional application No. 62/381,450, filed on Aug. 30, 2016.

(51) Int. Cl.
| | | |
|---|---|---|
| A61K 33/40 | (2006.01) | |
| A61K 47/10 | (2017.01) | |
| A61K 47/12 | (2006.01) | |
| D06B 1/02 | (2006.01) | |

(52) U.S. Cl.
CPC .............. *A61K 33/40* (2013.01); *A61K 47/10* (2013.01); *A61K 47/12* (2013.01); *D06B 1/02* (2013.01)

(58) Field of Classification Search
CPC ........ A61K 33/40; A61K 47/12; A61K 47/10; D06B 1/02
See application file for complete search history.

(56) References Cited

U.S. PATENT DOCUMENTS

| | | | |
|---|---|---|---|
| 3,194,768 A | 7/1965 | Linder et al. | |
| 4,113,645 A | 9/1978 | DeSimone | |
| 6,008,175 A | 12/1999 | Scialla et al. | |
| 6,096,348 A * | 8/2000 | Miner ............... | A01N 59/00 422/12 |
| 6,133,222 A | 10/2000 | Vinson et al. | |
| 6,468,954 B2 | 10/2002 | Levitt et al. | |
| 6,482,357 B1 | 11/2002 | Fox et al. | |
| 6,530,384 B1 | 3/2003 | Meyers et al. | |
| 6,566,574 B1 | 5/2003 | Tadros et al. | |
| 6,569,344 B1 | 5/2003 | Hubesch et al. | |
| 6,627,550 B2 | 9/2003 | Andreas | |
| 6,800,247 B1 | 10/2004 | Suh et al. | |
| 6,830,764 B2 | 12/2004 | Inui et al. | |
| 7,018,977 B2 | 3/2006 | Martens et al. | |
| 7,199,093 B2 | 4/2007 | Li et al. | |
| 7,862,623 B1 | 1/2011 | Hansen et al. | |
| 9,044,414 B2 | 6/2015 | Clark et al. | |
| 2002/0177540 A1 | 11/2002 | Masotti et al. | |
| 2003/0203035 A1 | 10/2003 | Hasan et al. | |
| 2003/0206965 A1* | 11/2003 | Hasan ................... | A61K 33/24 424/617 |
| 2005/0054702 A1 | 3/2005 | Dunn et al. | |
| 2005/0197319 A1 | 9/2005 | Nonomura et al. | |
| 2006/0030515 A1 | 2/2006 | Martens et al. | |
| 2007/0014687 A1 | 1/2007 | Tabor et al. | |
| 2009/0148342 A1* | 6/2009 | Bromberg ............. | A01N 59/00 422/37 |
| 2013/0183879 A1 | 7/2013 | Lee et al. | |
| 2014/0020711 A1 | 1/2014 | Kaser | |
| 2015/0086647 A1 | 3/2015 | Lakaye et al. | |
| 2015/0152364 A1 | 6/2015 | Theyssen et al. | |
| 2015/0259626 A1 | 9/2015 | Bureiko et al. | |

FOREIGN PATENT DOCUMENTS

| | | |
|---|---|---|
| EP | 0845526 | 6/1998 |
| WO | 2015164677 A1 | 10/2015 |

OTHER PUBLICATIONS

Raffellini, et al, "Effect of Hydrogen Peroxide Concentration and pH on Inactivation Kinectics of *Escherichia Coli*", Journal of Food Safety 28 (2008) 514-533.

\* cited by examiner

*Primary Examiner* — Blessing M Fubara
(74) *Attorney, Agent, or Firm* — Church & Dwight Co., Inc.

(57) ABSTRACT

The present disclosure provides compositions and methods useful in the deactivation of allergens. The compositions can comprise a peroxide and can particularly be at a relatively low pH (e.g., less than 5). The compositions exhibit efficacy for deactivation of a wide variety of allergens and are suitable for application to one or more types of surfaces to provide for deactivation of at least a portion of allergens present on the surface.

11 Claims, 19 Drawing Sheets

FIG. 5

Reducing Effects on Mus m 1 (10/90)

FIG. 6

Reducing Effects on Bet v 1 (10/90)

COMPOSITION AND METHOD FOR ALLERGEN DEACTIVATION

CROSS-REFERENCE TO RELATED APPLICATIONS

The present application claims priority to U.S. Provisional Pat. App. No. 62/381,450, filed Aug. 30, 2016, the disclosure of which is incorporated herein by reference.

FIELD OF THE DISCLOSURE

The present disclosure relates to compositions and methods of use thereof for deactivation of allergens. Anti-allergen compositions can be applied to a variety of surfaces so that contact with allergens thereon causes deactivation of at least a portion of the allergens.

BACKGROUND

Many people exhibit sensitivities to various allergens, and such sensitivities can result in allergic reactions ranging from mild to deadly. An allergen can be defined as any antigen producing an atypically aggressive immune response. An allergen specifically can stimulate a type-I hypersensitivity reaction where the immunoglobulin E response achieves levels typically only seen with a parasitic infection. Because of the prevalence of allergens in homes, businesses, and the like, it is desirable to reduce the allergen and thus limit allergenic reactions. Accordingly, there is a need for products that are effective for allergen deactivation and safe for use around people and animals.

SUMMARY OF THE DISCLOSURE

The present disclosure provides compositions effective for deactivation of allergens. The compositions can be applied to a variety of surfaces so as to come into direct contact with allergens present on the surface. Surface for application can be soft (e.g., textiles or other fiber-based articles) or hard (e.g., wood, stone, polymeric materials, and the like). Non-limiting examples of surfaces that can be subject to application of the anti-allergen compositions include upholstery, bedding, carpet, clothing, and flooring (including porous and non-porous materials).

In one or more embodiments, an anti-allergen composition according to the present disclosure can comprise a peroxide. In some embodiments, hydrogen peroxide in particular can be used. The peroxide can be effective to denature one or more allergens and otherwise render the one or more allergens non-allergenic. Conventional knowledge indicates that hydrogen peroxide become more active as the pH level increases into the alkaline range (particularly in the range of 6 to 12). At such pH, higher concentrations of the perhydroxyl anion understood to be the predominant oxidizer species for known uses of the material—e.g., stain and soil removal. Surprisingly, however, it has been found that peroxides can exhibit anti-allergen activities and that such activities can be increased by lowering the pH. Preferably, the anti-allergen compositions can have a pH of less than 5, such as in the range of about 1 to about 4.5, about 2 to about 4, or about 2.5 to about 3.5.

In one or more embodiments, the present disclosure thus can provide an anti-allergen composition comprising a peroxide, the composition having a pH of less than 5. In some embodiments, the composition can comprise about 0.1% to about 12% by weight, about 1% to about 10% by weight, about 1.5% to about 8% by weight, about 2% to about 6% by weight, or about 3% to about 5% by weight of the peroxide based on the total weight of the anti-allergen composition.

In some embodiments, the anti-allergen compositions can comprise added materials. For example, the anti-allergen composition can comprise a pH adjusting agent. Such pH adjusting agent preferably can be an acid and can be added in an amount suitable to adjust the pH to the range otherwise described herein. If desired, buffers or buffer systems can be utilized to achieve a desired pH and stabilize the composition within the desired range. As such, one or more basic materials may be included as needed to maintain a pH within the described range. The pH adjusting agent preferably is present in an amount suitable to maintain the desired pH range. For example, the pH adjusting agent can be present in an amount of about 0.05% to about 1%, about 0.08% to about 0.75%, or about 0.1% to about 0.5% by weight based on the total weight of the anti-allergen composition.

A variety of pH adjusting agents may be used. For example, organic acids may be used, such as citric acid, malic acid, gluconic acid, glutaric acid, and combinations thereof. Mineral acids, such as hydrochloric acid, sulfuric acid, or the like also may be used to adjust composition pH to the desired level but preferably only when used with a weak base (e.g., sodium citrate or sodium gluconate). Such combinations may be utilized to formulate a buffer system that is effective to maintain a sufficiently pH within the desired range.

In some embodiments, the anti-allergen composition can comprise a surfactant or a combination of surfactants. In particular, non-ionic surfactants may be used (although it is understood that cationic surfactants and/or anionic surfactants can be present or can be specifically excluded). In some embodiments, ethoxylated alcohols can be used. For example, C8-C10 linear alcohol ethoxylates, C9-C11 oxo alcohol ethoxylates, and similar nonionic surfactants may be used. In some embodiments, anionic surfactants with alkyl chain lengths of C6-C18 with or without aryl groups that are linear or branched, such as alkyl sulfates, alkyl and alkyl aryl sulfonates, and alkyl carboxylates may be used. Other suitable anionic surfactants include, for example, olefin sulfonates, including long-chain alkene sulfonates, long-chain hydroxyalkane sulfonates or mixtures of alkene sulfonates and hydroxyalkane sulfonates. In some embodiment, nonionic surfactants with alkyl chain lengths from C6-C18 with or without aryl groups that are linear or branched, such as ethoxylated alcohols, alkoxylated alcohols, alkyl polyglycosides, and alkyl amine oxides may be used. Other suitable water-soluble nonionic surfactants that may be used are marketed under the tradename Pluronic®. In some embodiments, cationic surfactants with alkyl chain lengths from C6-C18 with or without aryl groups that are linear or branched, such as primary alkyl amines, secondary alkyl amines, tertiary alkyl amines, and quaternary alkyl amines can be used. In some embodiments, zwitterionic and amphoteric surfactants with alkyl chain lengths from C6-C18 with or without aryl groups that are linear or branched, such as alkyl betaines, alkyl sulfo betaine, alkyl amino, or imino propionates can be used. Preferably, any surfactants that are utilized are stable in the pH ranges listed herein as well in the presence of the peroxide component. In one or more embodiments, quaternary surfactants may be included. Dodecyl trimethyl ammonium chloride ("DTAC") is one non-limiting example of a quaternary surfactant that may be utilized. Surfactants preferably are present in an amount of about 0.05% to about 5%, about 0.8% to about 4%, or about 1% to about 3% by weight based on the total weight of the composition.

Still further components may also be used as desired. For example, a non-allergenic fragrance may be added. Alternately or additionally, in order to promote cleaning and/or faster drying, a lower alcohol, such as ethanol, can be included. Further, as the anti-allergen compositions are preferably in the form of an aqueous solution, the balance of the anti-allergen composition after addition of all required ingredients preferably is water.

In some embodiments, the peroxide can be defined in terms of being an allergen deactivator. In this sense, the anti-allergen compositions of the present disclosure can comprise one peroxide compound or a plurality of peroxide compounds, and the peroxide compound or peroxide compounds can be the only allergen deactivator present in the anti-allergen compositions. As such, the anti-allergen compositions may consist essentially of the peroxide compound or compounds, and one or more adjuvants, the adjuvants being exemplified by the pH adjustors, the surfactants, the fragrance, and the water as discussed herein, as well as like materials that are not effective as an allergen deactivator. In some embodiments, an anti-allergen composition can consist of one or more peroxides, one or more pH adjustors, one or more surfactants, optional fragrance, and balance water.

In one or more embodiments, the present disclosure further can relate to methods for deactivating allergens on a substrate. Such methods can comprise applying an anti-allergen composition as described herein to the substrate in an amount effective to deactivate at least a portion of the allergens. The anti-allergen composition may be applied for a time of at least 5 minutes, at least 15 minutes, at least 30 minutes, at least one hour, at least 12 hours, or at least 24 hours. In some embodiments, the anti-allergen composition may be applied and allowed to dry. Drying may be achieved over a time of about 15 minutes to about 48 hours. The anti-allergen composition can be effective to reduce activity of one or more allergens over a defined time period (such as described herein) by about 20% or greater, about 30% or greater, about 50% or greater, about 75% or greater, about 90% or greater, or about 95% or greater. Such result can be achieved over a time period, in some embodiments, of about 5 minutes to about 48 hours, about 10 minutes to about 24 hours, about 15 minutes to about 12 hours, or about 30 minutes to about 8 hours.

In some embodiments, the anti-allergen composition can be applied by spraying, dipping, wiping, or any further mode effective to contact the allergens on the surface being treated. The composition thus can be in the form of a spray, an aerosol, a pump, or the like. Non-limiting examples of allergens subject to deactivation include a dust mite allergen, a cat allergen, a dog allergen, a mouse allergen, a pollen allergen, a grass allergen, a mold allergen, a nut allergen, and the like. The allergens in particular may be an antigen (e.g., a protein, a polysaccharide, or a lipid) originating from the noted source (e.g., from a dust mite, from a cat, from a dog, from a mouse, from pollen, from grass, from mold, from a nut, or the like), which antigen can cause an allergic response in a mammal, particularly in a human, the allergic response including but not limited to production of antibodies by the affected mammal. As illustrated by the testing described herein, the peroxide-based anti-allergen compositions described herein are effective as general, broad-spectrum anti-allergens.

BRIEF DESCRIPTION OF THE FIGURES

FIG. 5 is a graph showing the ability of a test formulation to deactivate Mus m1 allergen in a 90/10 (formulation to allergen ratio) volume solution;

FIG. 6 is a graph showing the ability of a test formulation to deactivate Bet v1 allergen in a 90/10 (formulation to allergen ratio) volume solution;

FIG. 26A is a graph showing the ability of a test formulation to deactivate Bet v1 on a fabric substrate 2 hours after application;

FIG. 26B is a graph showing the ability of a test formulation to deactivate Bet v1 on a fabric substrate 12 hours after application;

DETAILED DESCRIPTION OF THE DISCLOSURE

Figure 1:
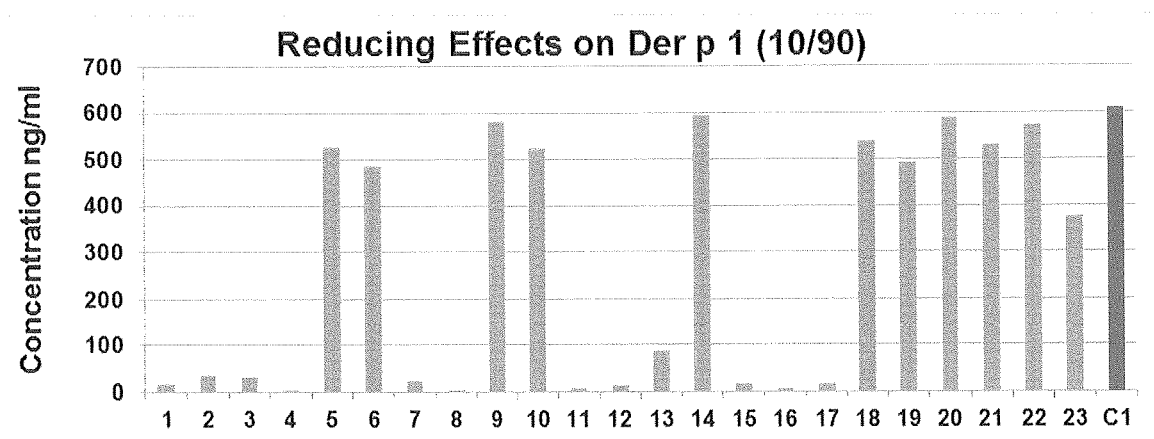
FIG. 1 is a graph showing the ability of a test formulation to deactivate Der p1 allergen in a 90/10 (formulation to allergen ratio) volume solution.

The invention now will be described more fully hereinafter through reference to various embodiments. These embodiments are provided so that this disclosure will be thorough and complete, and will fully convey the scope of the invention to those skilled in the art. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present disclosure relates to anti-allergen compositions and methods of use of such compositions to reduce the amount of one or more allergens present within a treatment area. The compositions can be applied directly to a surface having allergens present thereon. In some embodiments, however, the anti-allergen compositions may be administered as a general room spray so as to trap allergens in the air and/or result in a general coating on surfaces present in the room (e.g., furniture, carpeting, flooring, etc.). Example compositions suitable for use according to the present disclosure are shown below in TABLE 1.

TABLE 1

| Ingredient | Formula 1 (pH 2-4) | Formula 2 (pH 2-4) |
| --- | --- | --- |
| DI Water | QS to 100 wt. % | QS to 100 wt. % |
| Citric Acid | 0.1-0.5 wt. % | 0-0.5 wt. % |
| Hydrogen Peroxide | 2.0-6.0 wt. % | 0.5-6.0 wt. % |
| Nonionic surfactant | 0.1-2.0 wt. % | 0-2.0 wt. % |
| Quaternary Surfactant | — | 0.1-2.0 wt. % |
| Calcium Salt | — | 0-0.5 wt. % |
| Fragrance | 0-0.5 wt. % | 0-0.5 wt. % |

Anti-allergen compositions according to the present disclosure can comprise a peroxide and an aqueous carrier, the composition having a pH of less than 5. In some embodiments, the anti-allergen composition can comprise about 1% to about 12% peroxide based on the weight of the composition and have a pH of less than 5. In further embodiments, the anti-allergen composition can comprise about 2% to about 6% peroxide based on the weight of the composition and have a pH of about 2 to about 4. In some embodiments, the anti-allergen composition can comprise about 2.5% to about 5.5% peroxide based on the weight of the composition and have a pH of about 2.5 to about 3.5. In some embodiments, the anti-allergen composition can comprise peroxide as noted above with a pH as noted above and also include a pH adjusting agent (e.g., an organic acid) in an amount effective to maintain the noted pH range, such as an amount of about 0.05% to about 1%, about 0.08% to about 0.75%, or about 0.1% to about 0.5% by weight based on the total weight of the composition. In some embodiments, the anti-allergen composition can comprise peroxide and a pH adjusting agent as noted above with a pH as noted above and also include a surfactant in an amount of about 0.05% to about 5%, about 0.08% to about 4%, about 0.1% to about 3%, or about 0.2% to about 1% by weight based on the total weight of the composition.

The anti-allergen compositions are surprisingly effective against a broad spectrum of different allergens. Likewise, the anti-allergen compositions are amenable for use on a wide variety of substrates. As such, the present disclosure particularly can relate to a method for deactivating allergens on a substrate, the method comprising applying to the substrate an anti-allergen composition as described herein in an amount effective to deactivate at least a portion of the allergens present on the substrate. An effective amount can be an amount suitable so that the allergen is contacted directly by the anti-allergen composition. Preferably, the anti-allergen composition will be applied in an amount effective to wet at least a portion of an outer surface of the allergen. In some embodiments, an outer surface of the allergen can be substantially coated or completely coated with the anti-allergen composition.

In some embodiments, the substrate particularly can be a fibrous material, which can be a material that is formed from natural and/or synthetic fibers—e.g., textiles. More particularly, a fibrous material may be one or more of upholstery, carpeting, draperies, or clothing. In some embodiments, the substrate particularly can be a hard surface, such as an object formed from wood, stone, ceramic, vinyl, or a laminate. In general, the anti-allergen compositions of the present disclosure are suitable for use on substantially all surfaces on which allergens may reside and from which humans or animals may otherwise come into contact with the allergens. The anti-allergen compositions are suitable for application directly to the surface on which the allergen may be present, and the compositions may be allowed to remain on the surface, or the compositions may be wiped from the surface. Even when wiped away, the anti-allergen compositions of the present disclosure can be effective to deactivate allergens that may be removed with the wiping as well as allergens that may remain on a surface after wiping. Thus, efficacy of the present compositions is not limited to the ability to facilitate removal of the allergens. Rather, the compositions are effective to deactivate allergens on all surfaces and substrates contacted by the compositions.

The efficacy of the anti-allergen compositions against multiple different allergens is seen in the testing provided below, which showed efficacy in a solution environment as well as efficacy in relation to surface application of the anti-allergen compositions to multiple different types of surfaces. The testing encompassed multiple types of specific dust mite allergens, a specific cat allergen, a specific dog allergen, a specific mouse allergen, a specific pollen allergen, a specific grass allergen, multiple specific mold allergens, and a specific nut allergen. The chosen allergens are representative of other allergens from the same sources (e.g., other cat or dog allergens) as well as other allergens from different sources (e.g., allergens from other types of animals or other plant species). The cross-section of tested allergens is representative and shows that the present anti-allergen composition is effective against a broad spectrum of allergens and that there thus would be a reasonable expectation of deactivating other allergens than just the specific allergens tested herein with only minimal testing required to confirm the deactivation ability.

EXAMPLE 1

A series of studies was performed in order to assess the efficacy of various treatments against allergens in solution. Allergens used as targets in the testing are in TABLE 2 below.

TABLE 2

| Allergen Source | Allergen Name |
| --- | --- |
| Dust Mite | Der p1 |
| Dust Mite | Der f1 |
| Cat | Fel d1 |
| Dog | Can f1 |
| Mouse | Mus m1 |
| Birch Pollen | Bet v1 |
| Timothy Grass | Phl p5 |
| Alternaria Mold | Alt a1 |
| Aspergillus Mold | Asp f1 |
| Peanut | Ara h6 |

A total of 23 different compositions were tested against the allergen samples to identify activity. The tested compositions are shown in TABLE 3 below. The compositions were formed using a 50% $H_2O_2$ active stock solution. A 0.5% (w/v) solution of citric acid/citrate buffer ("Hcit") was used as the balance unless otherwise indicated to provide the water and pH adjuster. All percentages in TABLE 3 are w/v unless otherwise indicated. The ethoxylated alcohol surfactant used is commercially available under the name TOM-ADOL® 91-8. Aegis silane quaternary AEM 5772 referenced in TABLE 3 was formed of 12 wt. % methyl alcohol, 72 wt. % octadecyl amino dimethyl trimethoxysilyl propyl ammonium chloride, 15 wt. % chloropropyltrimethoxysilane, and 1 wt. % dimethyl octadecylamine.

TABLE 3

| Formula | Description | pH |
| --- | --- | --- |
| 1 | Commercial Pet Stain & Odor Spray | 5.0 |
| 2 | Commercial Pet Stain & Odor Spray (no $H_2O_2$) | 5.0 |
| 3 | 2.0% $H_2O_2$; qs Hcit | 3.06 |
| 4 | 5.0% $H_2O_2$; qs Hcit | 3.08 |
| 5 | 2.0% $H_2O_2$; qs Hcit | 4.92 |
| 6 | 5.0% $H_2O_2$; qs Hcit | 4.98 |
| 7 | 2.0% $H_2O_2$; 0.2% ethoxylated alcohol surfactant; qs Hcit | 3.03 |
| 8 | 5.0% $H_2O_2$; 0.2% ethoxylated alcohol surfactant; qs Hcit | 2.96 |
| 9 | 2.0% $H_2O_2$; 0.2% ethoxylated alcohol surfactant; qs Hcit | 4.94 |
| 10 | 5.0% $H_2O_2$; 0.2% ethoxylated alcohol surfactant; qs Hcit | 4.93 |
| 11 | 4.0% $H_2O_2$; qs Hcit | 3.04 |
| 12 | 4.0% $H_2O_2$; 0.2% ethoxylated alcohol surfactant; qs Hcit | 3.19 |
| 13 | 100% Hcit | 2.96 |
| 14 | 100% Hcit | 5.01 |
| 15 | 2.0% $H_2O_2$; 1.037% lauryl amine oxide; qs Hcit | 3.06 |
| 16 | 2.0% $H_2O_2$; 1.19% dodecyl trimethyl ammonium chloride; qs Hcit | 2.99 |
| 17 | 2.0% $H_2O_2$; 0.518% lauryl amine oxide; 0.594% dodecyl trimethyl ammonium chloride; qs Hcit | 2.99 |
| 18 | 1% Aegis silane quaternary AEM 5772 | 4.56 |
| 19 | Commercial Fabric & Carpet Foam Deodorizer | 8.0 |
| 20 | Commercial Allergen Reducer | 5.0 |
| 21 | 1% Enzyme NS-16768; 99% 0.05M Tris | 8.20 |
| 22 | 1% Enzyme NS-16679; 99% 0.05M Tris | 8.20 |
| 23 | 1% Enzyme NS-16769; 99% 0.05M Tris | 8.20 |

Levels of allergen activity were determined via Multiplex Array for Indoor Allergens (MARIA®). The MARIA® allergen detection technology utilizes fluorescent microspheres coupled with allergen specific monoclonal antibodies, which allows the simultaneous detection of multiple allergens in a single test with increased sensitivity and improved reproducibility compared to ELISA assays.

Figure 2:
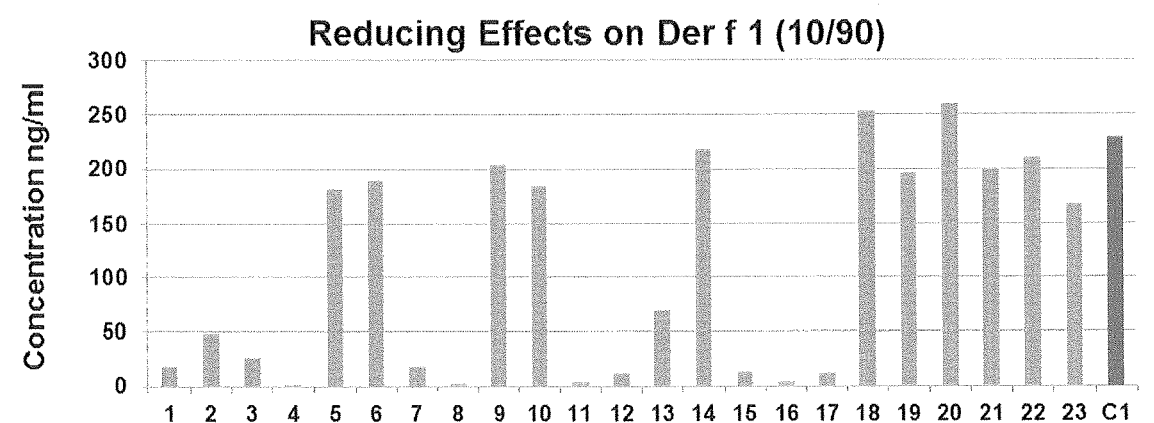
FIG. 2 is a graph showing the ability of a test formulation to deactivate Der f1 allergen in a 90/10 (formulation to allergen ratio) volume solution.
Figure 3:
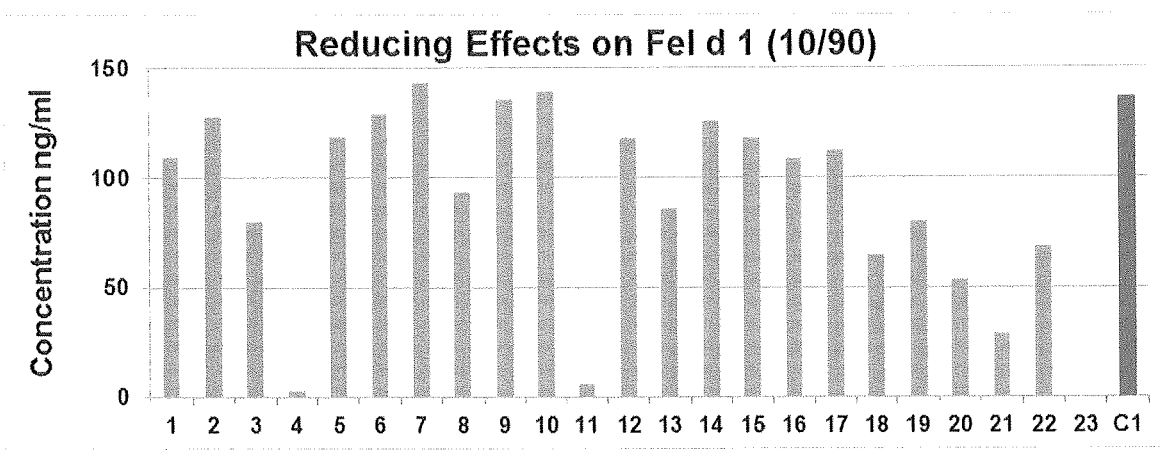
FIG. 3 is a graph showing the ability of a test formulation to deactivate Fel d1 allergen in a 90/10 (formulation to allergen ratio) volume solution.
Figure 4:
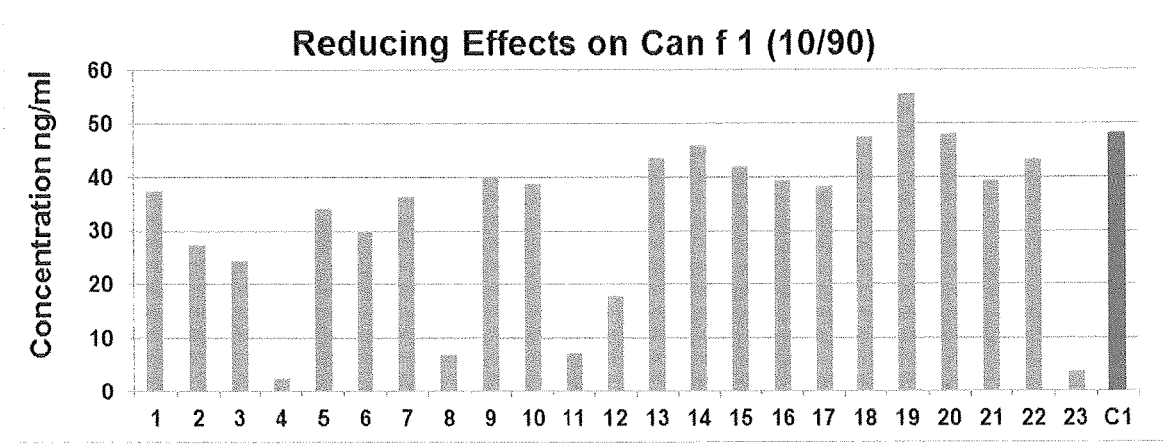
FIG. 4 is a graph showing the ability of a test formulation to deactivate Can f1 allergen in a 90/10 (formulation to allergen ratio) volume solution.
Figure 7:
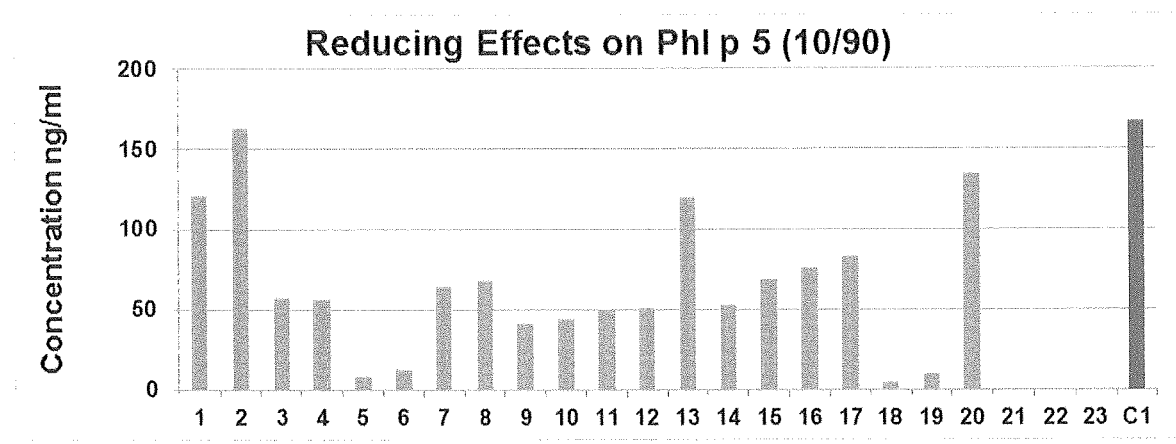
FIG. 7 is a graph showing the ability of a test formulation to deactivate Phi p5 allergen in a 90/10 (formulation to allergen ratio) volume solution.
Figure 8:
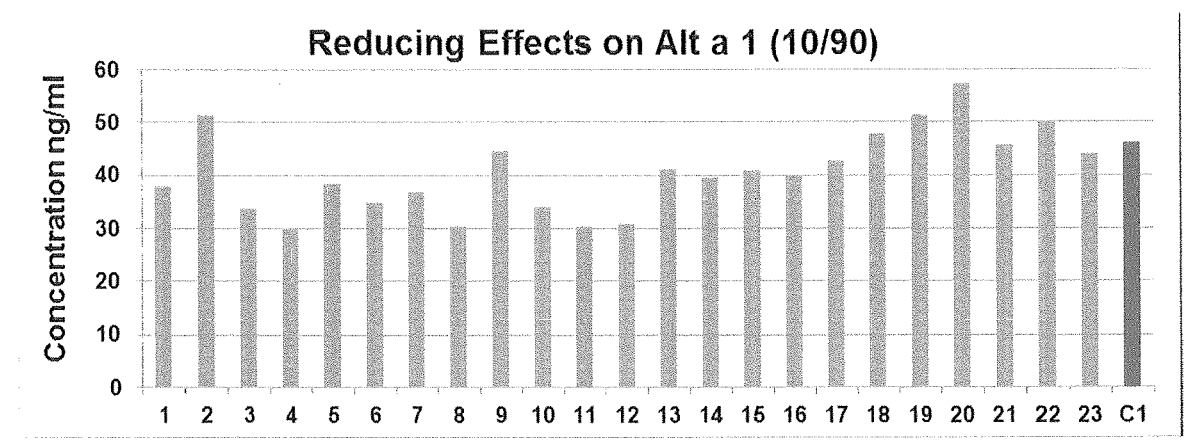
FIG. 8 is a graph showing the ability of a test formulation to deactivate Alt a1 allergen in a 90/10 (formulation to allergen ratio) volume solution.
Figure 9:
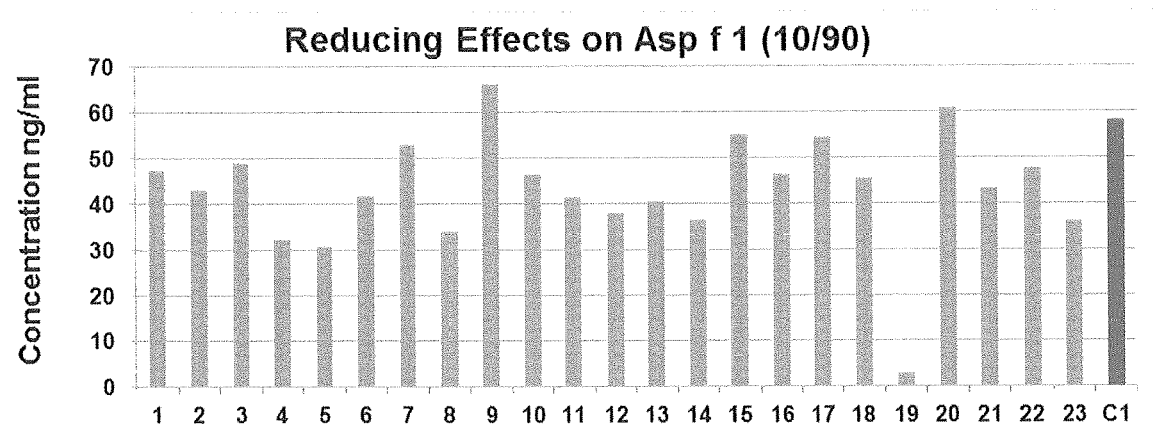
FIG. 9 is a graph showing the ability of a test formulation to deactivate Asp f1 allergen in a 90/10 (formulation to allergen ratio) volume solution.
Figure 10:
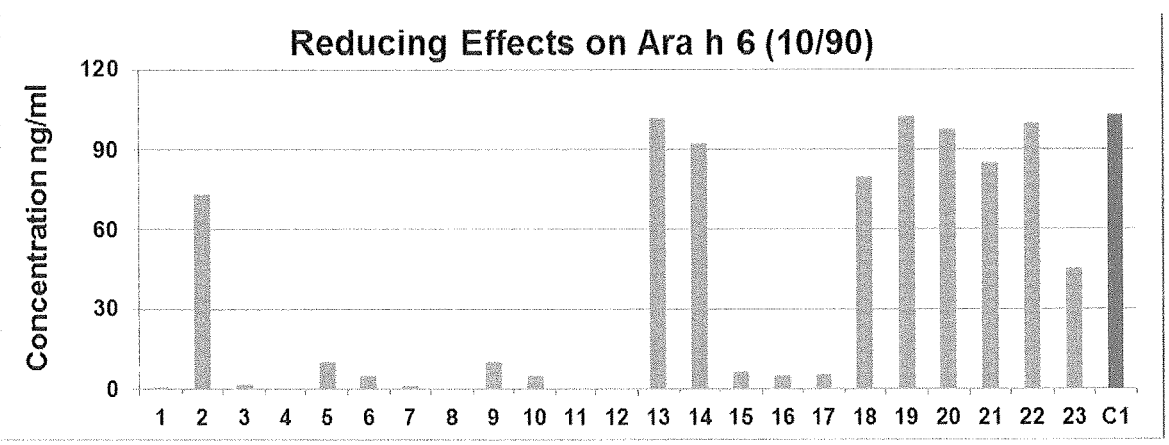
FIG. 10 is a graph showing the ability of a test formulation to deactivate Ara h6 allergen in a 90/10 (formulation to allergen ratio) volume solution.

Allergen extracts listed in TABLE 2 were mixed individually with 90% total volume of each formula from TABLE 3 and left to incubate while rocking for 2 hours. All samples were analyzed using MARIA® to compare the allergen reducing effects of the each of the Formulas individually versus the control. The allergen contents of the samples were expressed as ng/ml and the reducing effects as a % reduction compared to the concentration of the control samples. Efficacy plots for the reducing effects of each Formula against the ten tested allergens are shown in FIG. 1 through FIG. 10. As seen therein, Formulas including the peroxide at pH 3 (see, e.g., Formula 3, Formula 4, Formula 7, and Formula 8) exhibited very good efficacy in deactivating a wide number of different allergens. Surprisingly, when the pH was increased (see, e.g., Formula 5, Formula 6, Formula 9, and Formula 10), the efficacy of allergen deactivation decreased.

EXAMPLE 2

Based on results from testing in EXAMPLE 1 of the ability of certain systems to deactivate allergens in solution, compositions were tested for their effectiveness against allergens in specific use actions. These modes included treatment of carpet, treatment of fabric, and hard surface cleaning. The compositions tested are shown below in TABLE 4. The compositions were formed using a 50% $H_2O_2$ active stock solution. A 0.5% Hcit solution was again used as the balance unless otherwise indicated to provide the water and pH adjuster. All percentages in TABLE 4 are w/v unless otherwise indicated. The ethoxylated alcohol surfactant used is commercially available under the name TOM-ADOL® 91-8. Allergens used as targets in the testing are shown in TABLE 5.

TABLE 4

| Formula | Description | pH |
|---|---|---|
| 1 | 5.0% $H_2O_2$; qs Hcit | 3.0 |
| 2 | 4.0% $H_2O_2$; qs Hcit | 3.0 |
| 3 | 2.0% $H_2O_2$; qs Hcit | 3.0 |
| 4 | 5.0% $H_2O_2$; 0.3% ethoxylated alcohol surfactant; qs Hcit | 3.0 |
| 5 | 2.0% $H_2O_2$; 0.3% ethoxylated alcohol surfactant; qs Hcit | 3.0 |
| 6 | 1.2% DTAC; ; 3.16% calcium acetate; qs DI water | 7.8 |
| 7 | Commercial Allergen Reducer | 5.0 |
| 8 | Commercial Fabric & Carpet Foam Deodorizer | 8.0 |
| 9 | 5.0% $H_2O_2$; 0.3% ethoxylated alcohol surfactant; qs Hcit | 3.0 |
| 10 | 4.0% $H_2O_2$; 0.3% ethoxylated alcohol surfactant; qs Hcit | 3.0 |
| 11 | 2.0% $H_2O_2$; 0.3% ethoxylated alcohol surfactant; qs Hcit | 3.0 |
| 12 | 1.2% DTAC; ; 3.16% calcium acetate; qs DI water | 7.8 |
| 13 | Commercial Daily Floor Cleaner | — |
| 14 | Commercial Aerosol Dust Remover | — |
| 15 | Commercial mopping wet pad | — |

TABLE 5

| Allergen Source | Allergen Name |
|---|---|
| Dust Mite | Der p1 |
| Dust Mite | Der f1 |
| Cat | Fel d1 |
| Dog | Can f1 |
| Mouse | Mus m1 |
| Birch Pollen | Bet v1 |
| Timothy Grass | Phl p5 |
| Alternaria Mold | Alt a1 |
| Peanut | Ara h6 |

Carpet Testing

Squares of a short pile polyolefin carpet were cut to dimensions 2 in.×2 in. The squares were inoculated with 1 mL of a concentrated allergen extract. The squares were allowed to dry for two hours. The squares were then treated with 9 mL of test product (Formulas 1 through 8) or deionized water. The squares were then allowed to sit for 2, 12, or 24 hours, and then extracted with buffer solution.

Figure 11:
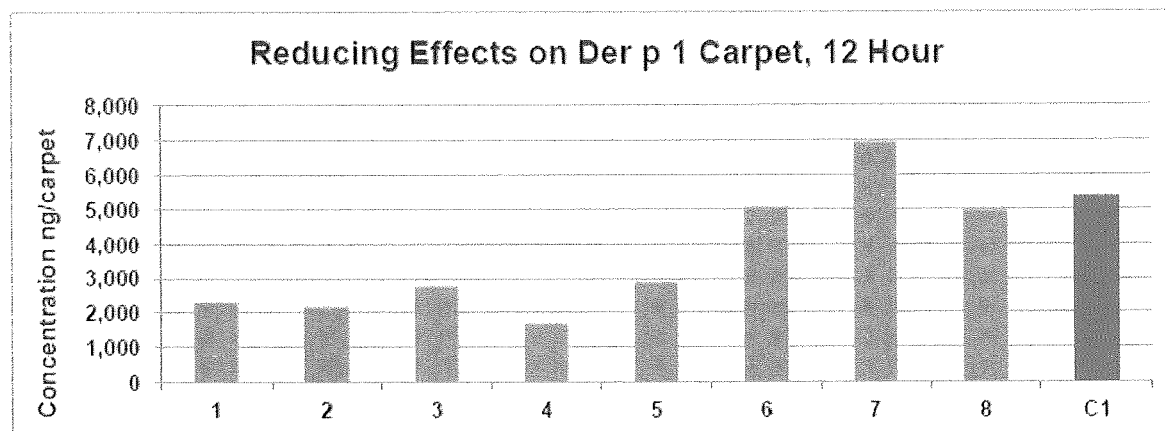
FIG. 11 is a graph showing the ability of a test formulation to deactivate Der p1 on a carpet substrate 12 hours after application.
Figure 12:
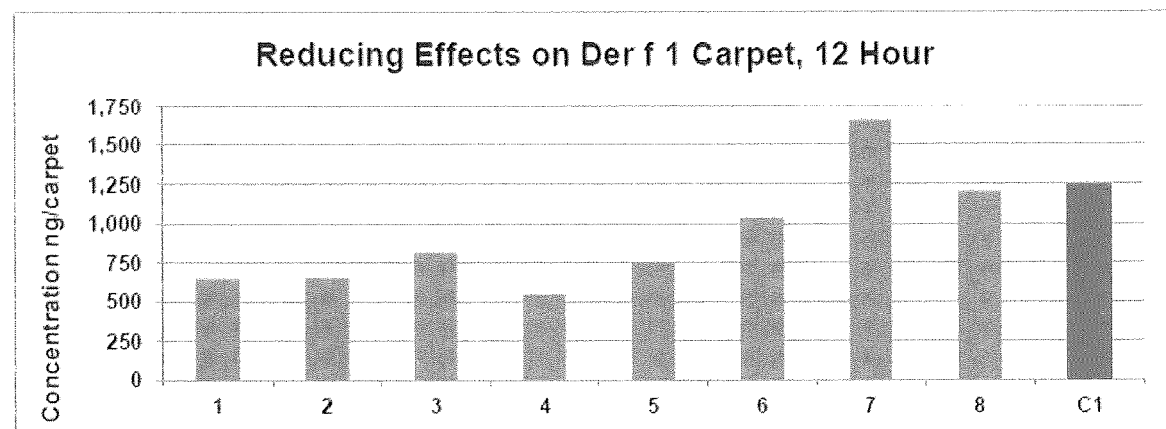
FIG. 12 is a graph showing the ability of a test formulation to deactivate Der f1 on a carpet substrate 12 hours after application.
Figure 13:
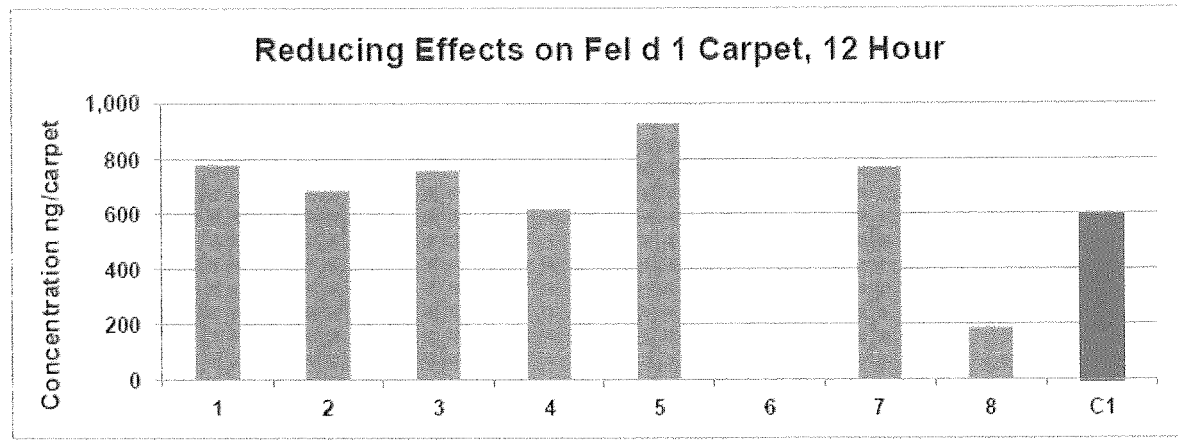
FIG. 13 is a graph showing the ability of a test formulation to deactivate Fel d1 on a carpet substrate 12 hours after application.
Figure 14:
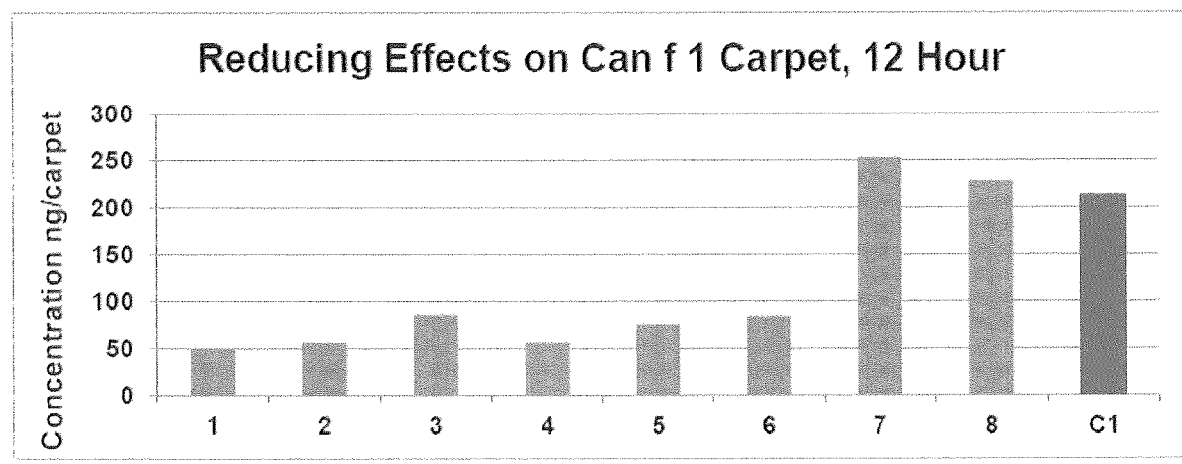
FIG. 14 is a graph showing the ability of a test formulation to deactivate Can f1 on a carpet substrate 12 hours after application.
Figure 15:
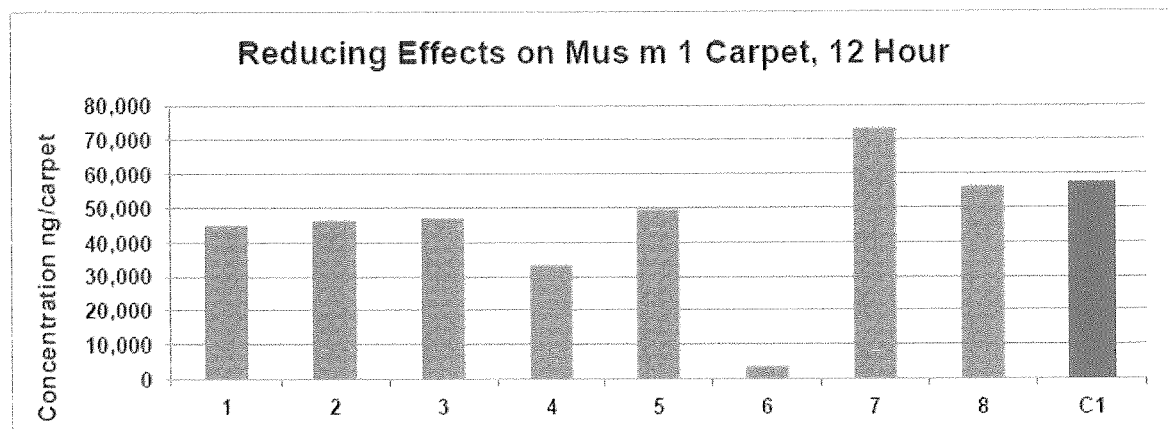
FIG. 15 is a graph showing the ability of a test formulation to deactivate Mus m1 on a carpet substrate 12 hours after application.
Figure 16:
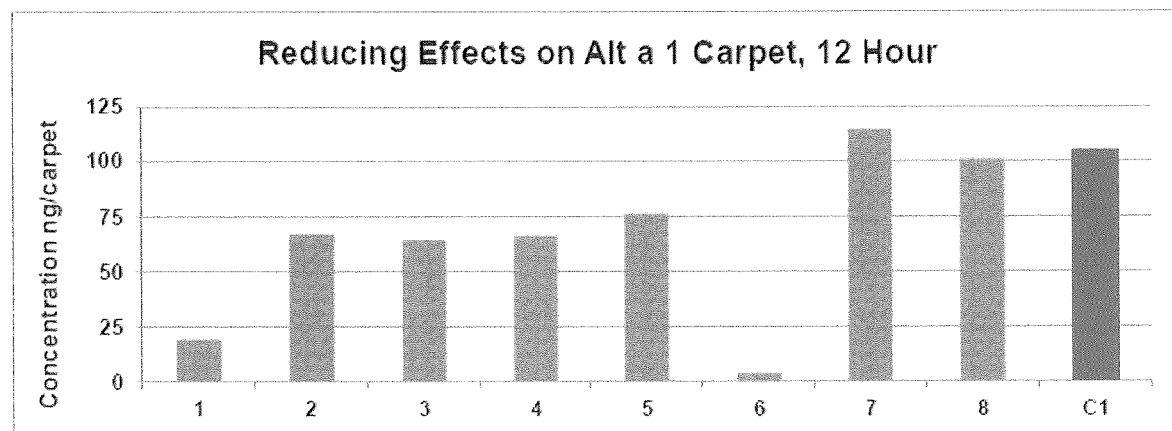
FIG. 16 is a graph showing the ability of a test formulation to deactivate Alt a1 on a carpet substrate 12 hours after application.
Figure 17:
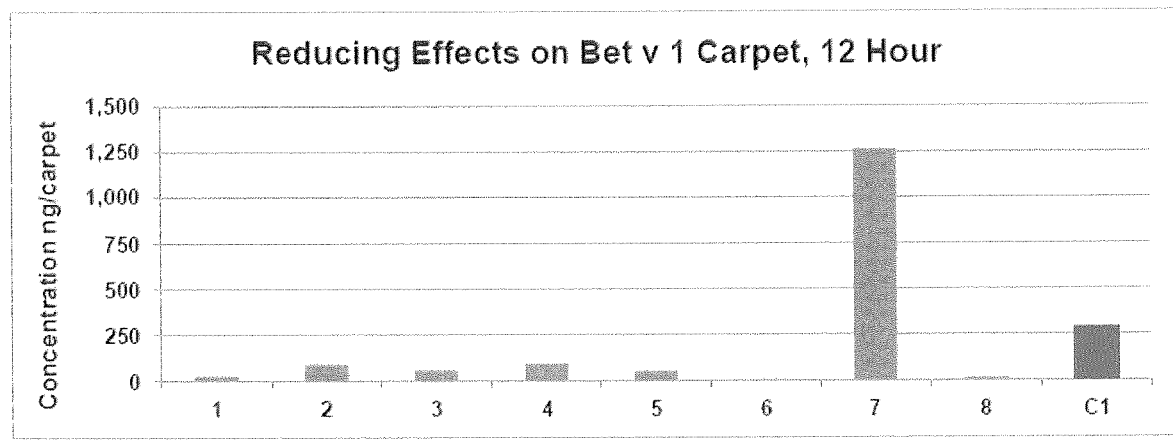
FIG. 17 is a graph showing the ability of a test formulation to deactivate Bet v1 on a carpet substrate 12 hours after application.
Figure 18:
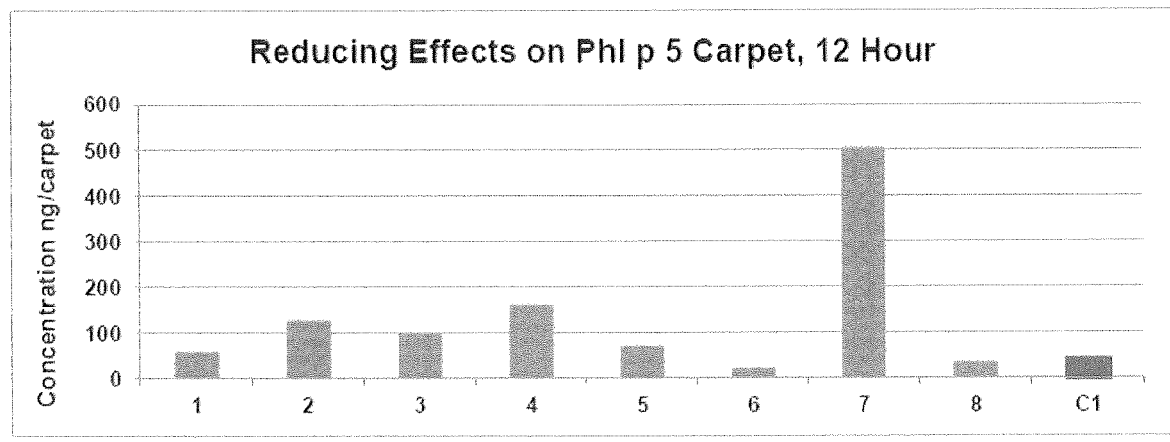
FIG. 18 is a graph showing the ability of a test formulation to deactivate Phi p5 on a carpet substrate 12 hours after application.
Figure 19:
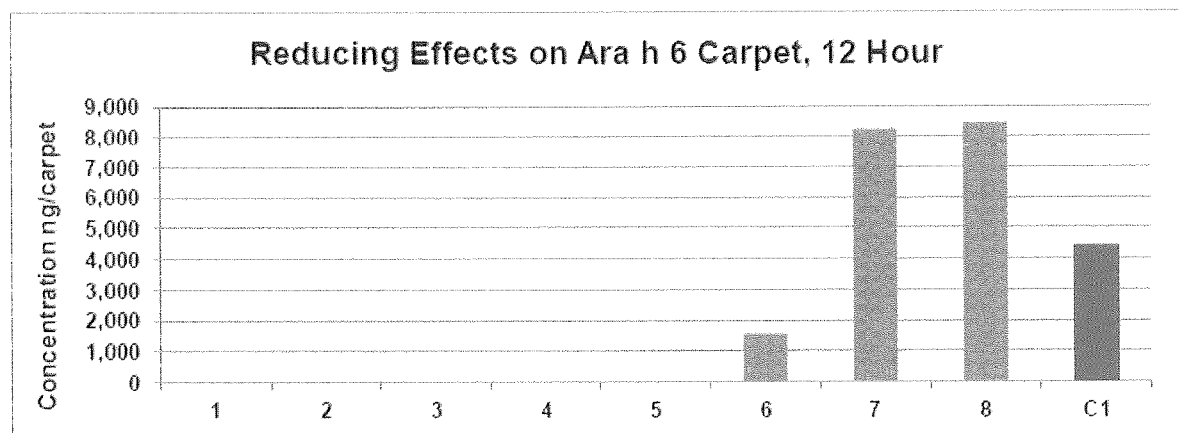
FIG. 19 is a graph showing the ability of a test formulation to deactivate Ara h6 on a carpet substrate 12 hours after application.

Levels of allergen activity were again determined via MARIA® allergen detection. In consideration of results at 2, 12, and 24 hours, trends were similar between the three different time frames, although significant differentiation was typically seen at 12 hours. Said 12 hour data is illustrated in FIG. 11 through FIG. 19 and shows data indicating concentration of allergen detected for the treatments and for the water control ("C1").

Fabric Testing

Squares of cotton fabric were cut to dimensions 2 in.–2 in. The squares were inoculated with 1 mL of a concentrated allergen extract. The squares were allowed to dry for two hours. The squares were then treated with 9 mL of test product (Formulas 1 through 8) or deionized water. The squares were then allowed to sit for 2, 12, or 24 hours, and then extracted with buffer solution.

Figure 20A:
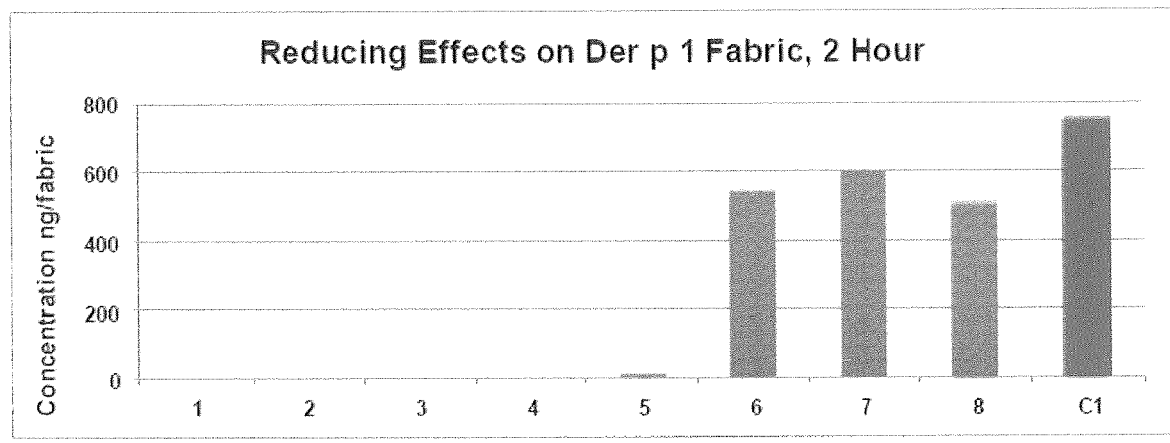
FIG. 20A is a graph showing the ability of a test formulation to deactivate Der p1 on a fabric substrate 2 hours after application.
Figure 20B:
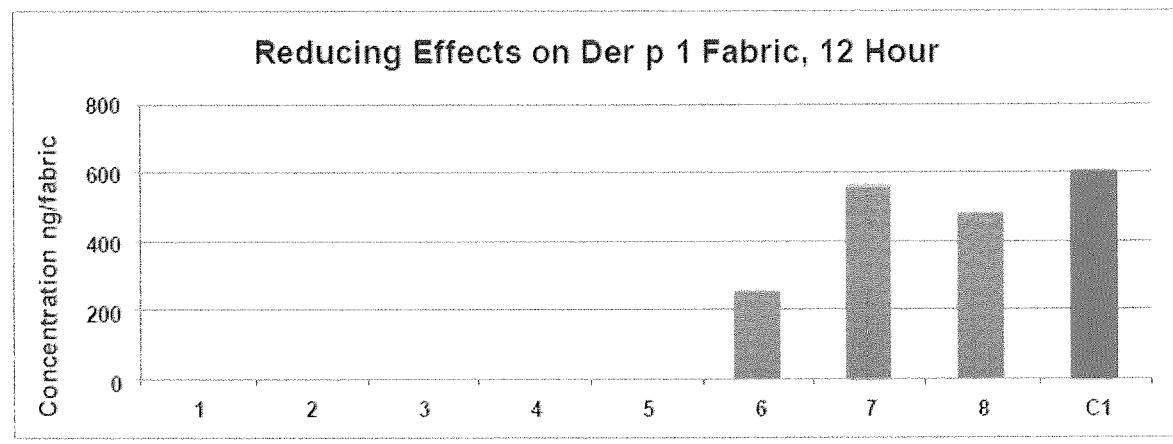
FIG. 20B is a graph showing the ability of a test formulation to deactivate Der p1 on a fabric substrate 12 hours after application.
Figure 21A:
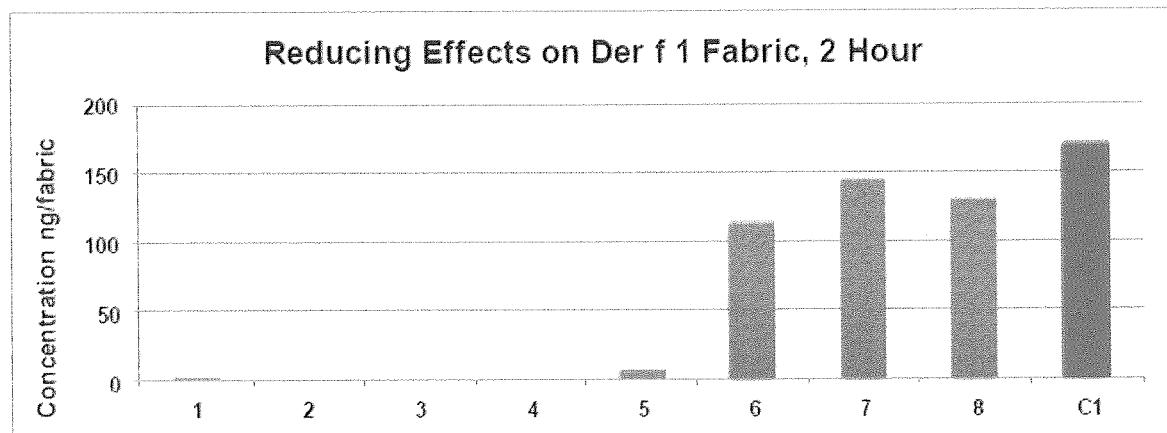
FIG. 21A is a graph showing the ability of a test formulation to deactivate Der f1 on a fabric substrate 2 hours after application.
Figure 21B:
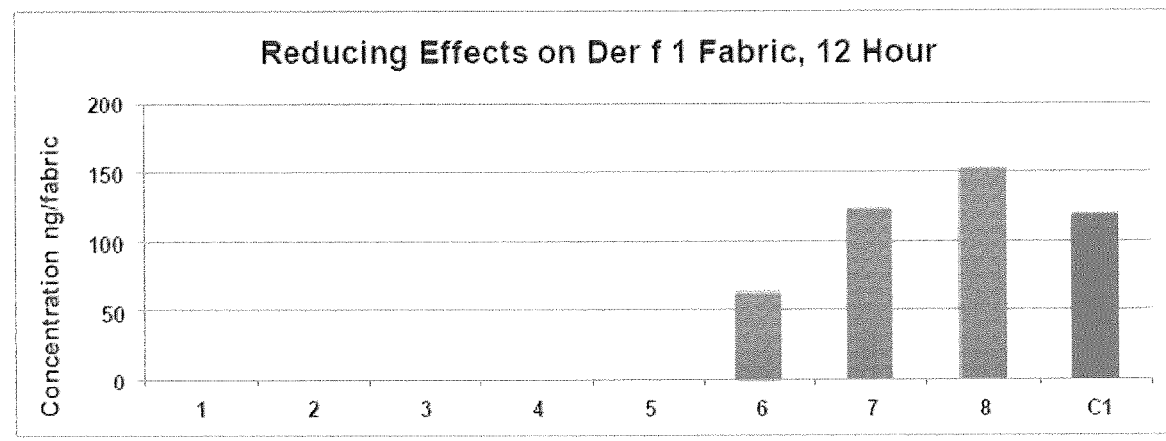
FIG. 21B is a graph showing the ability of a test formulation to deactivate Der f1 on a fabric substrate 12 hours after application.
Figure 22A:
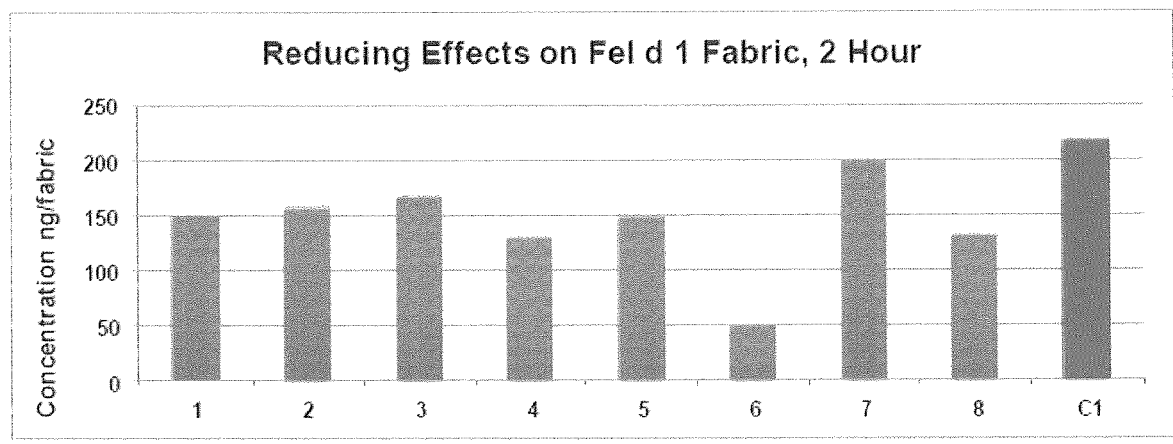
FIG. 22A is a graph showing the ability of a test formulation to deactivate Fel d1 on a fabric substrate 2 hours after application.
Figure 22B:
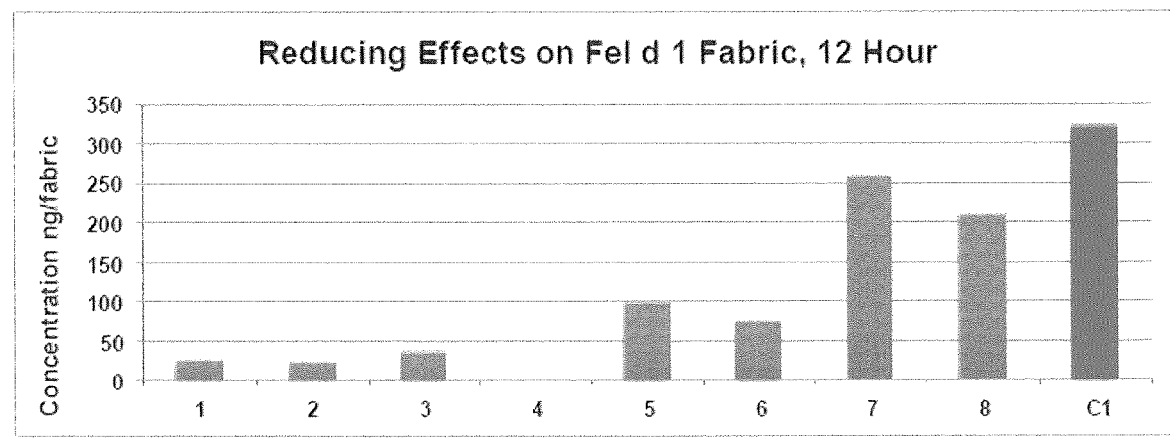
FIG. 22B is a graph showing the ability of a test formulation to deactivate Fel d1 on a fabric substrate 12 hours after application.
Figure 23A:
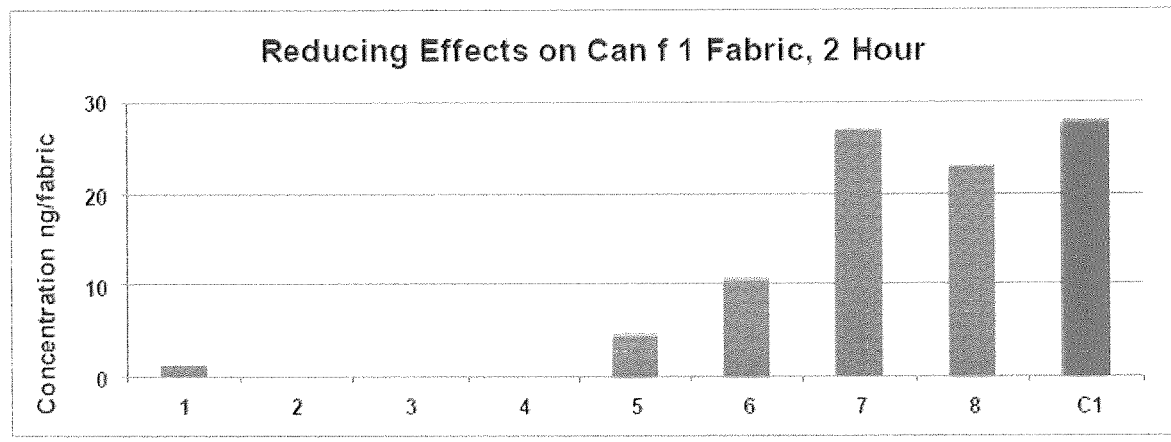
FIG. 23A is a graph showing the ability of a test formulation to deactivate Can f1 on a fabric substrate 2 hours after application.
Figure 23B:
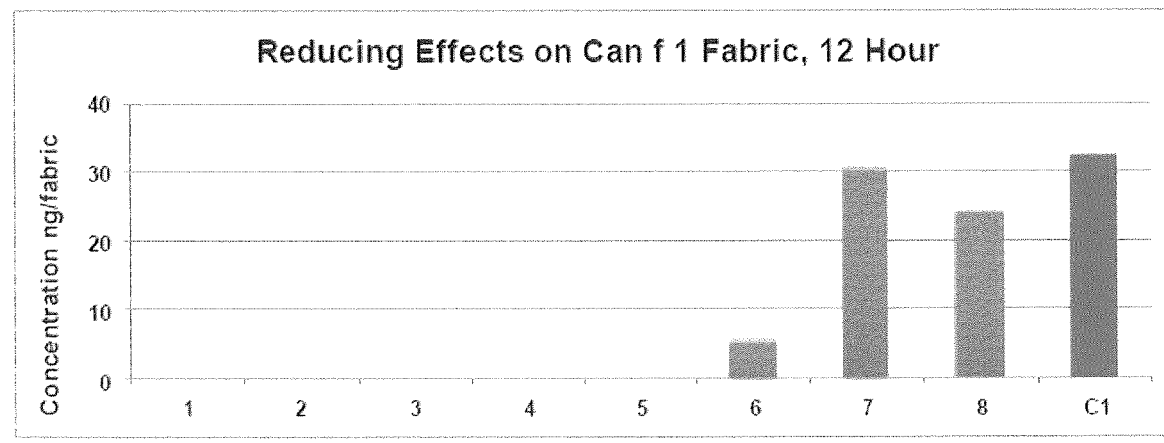
FIG. 23B is a graph showing the ability of a test formulation to deactivate Can f1 on a fabric substrate 12 hours after application.
Figure 24A:
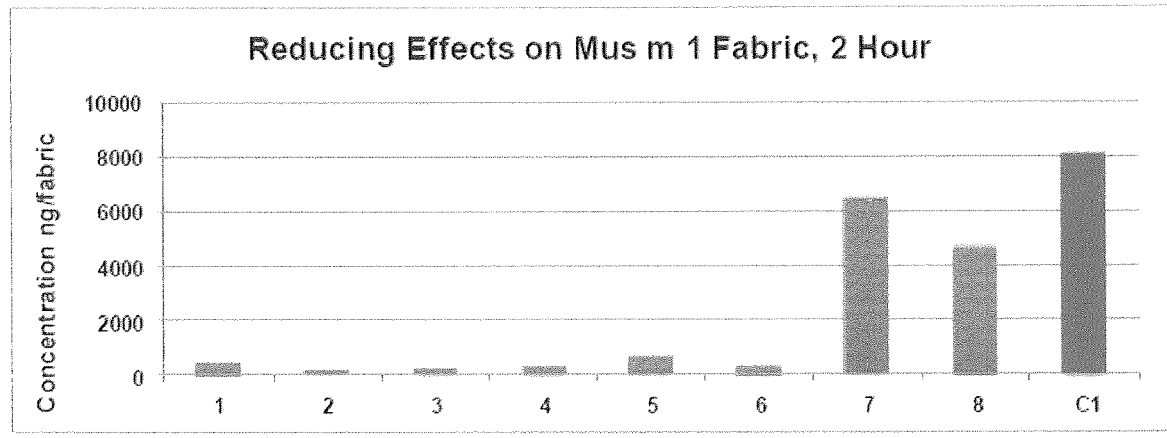
FIG. 24A is a graph showing the ability of a test formulation to deactivate Mus m1 on a fabric substrate 2 hours after application.
Figure 24B:
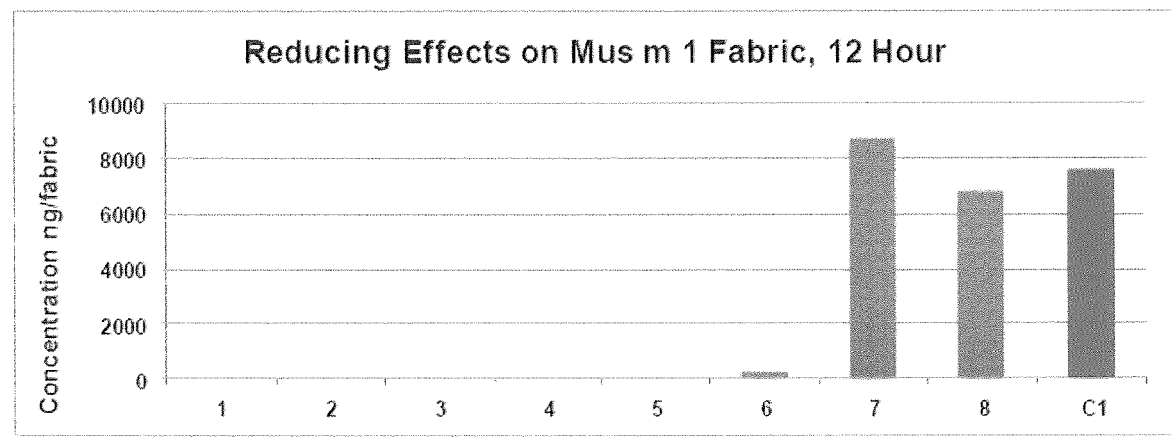
FIG. 24B is a graph showing the ability of a test formulation to deactivate Mus m1 on a fabric substrate 12 hours after application.
Figure 25A:
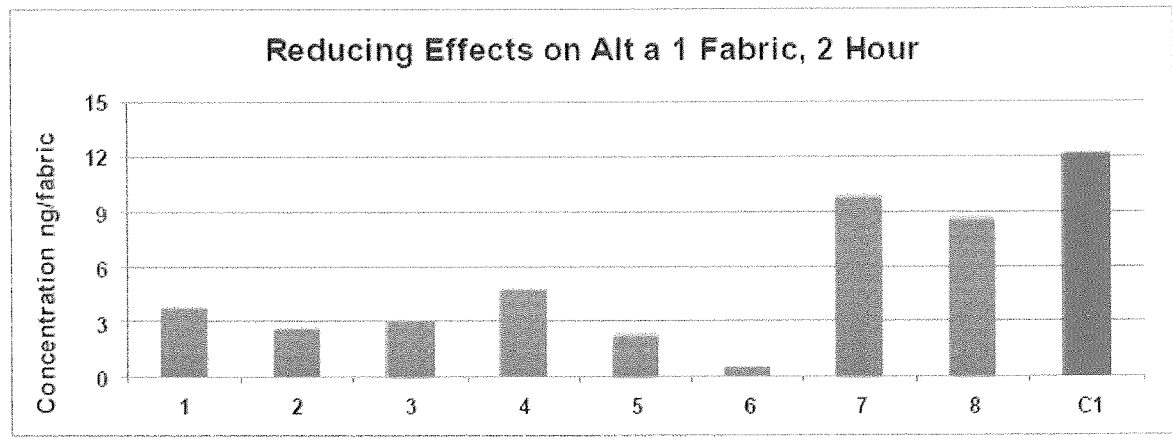
FIG. 25A is a graph showing the ability of a test formulation to deactivate Alt a1 on a fabric substrate 2 hours after application.
Figure 25B:
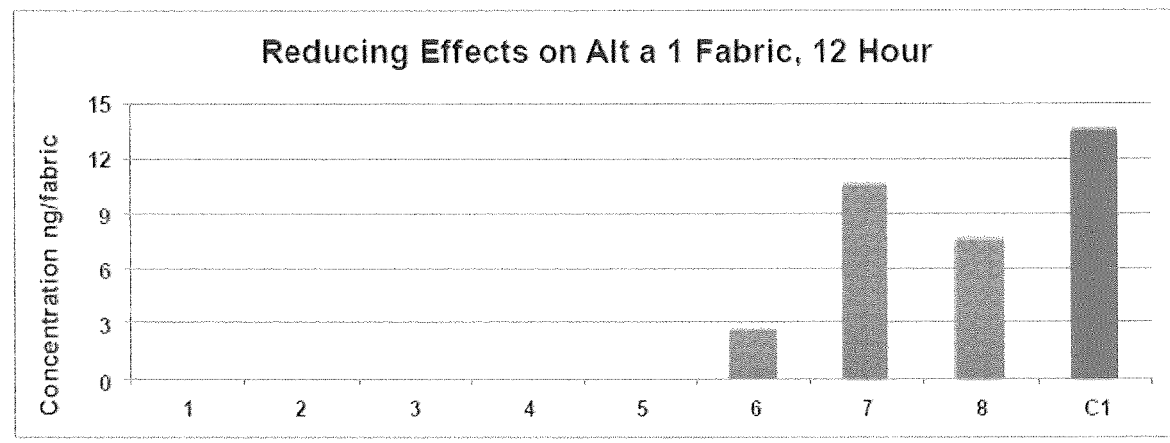
FIG. 25B is a graph showing the ability of a test formulation to deactivate Alt a1 on a fabric substrate 12 hours after application.
Figures 26A, 26B:
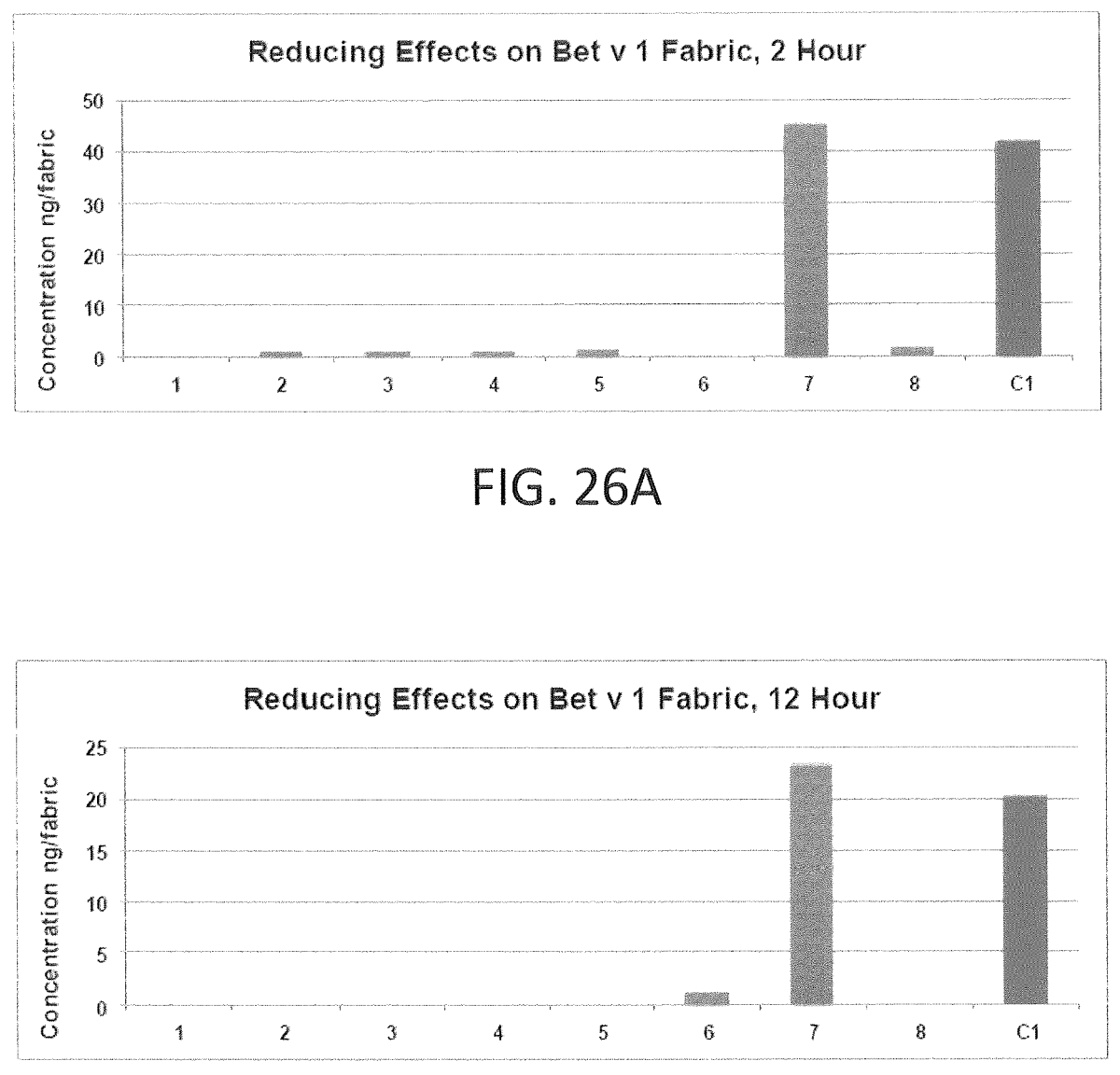
Figure 27A:
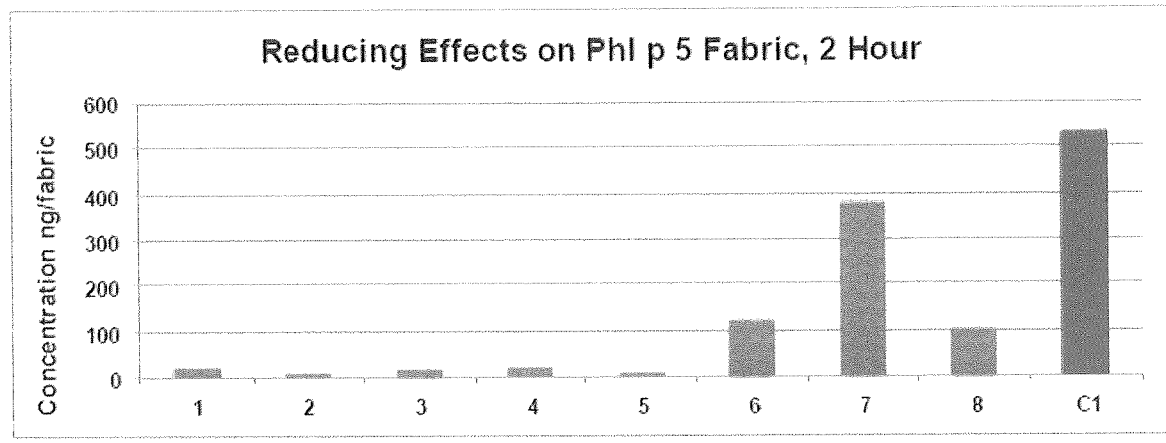
FIG. 27A is a graph showing the ability of a test formulation to deactivate Phi p5 on a fabric substrate 2 hours after application.
Figure 27B:
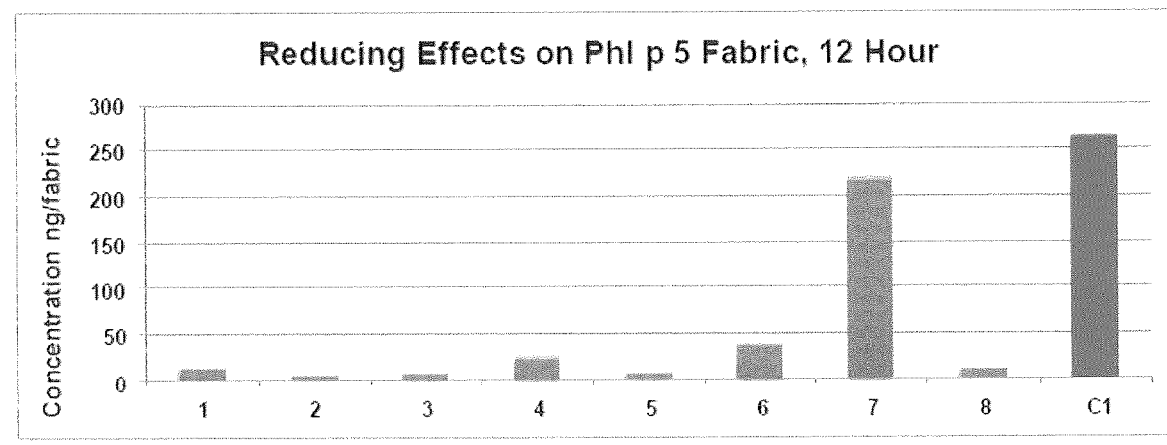
FIG. 27B is a graph showing the ability of a test formulation to deactivate Phi p5 on a fabric substrate 12 hours after application.
Figure 28A:
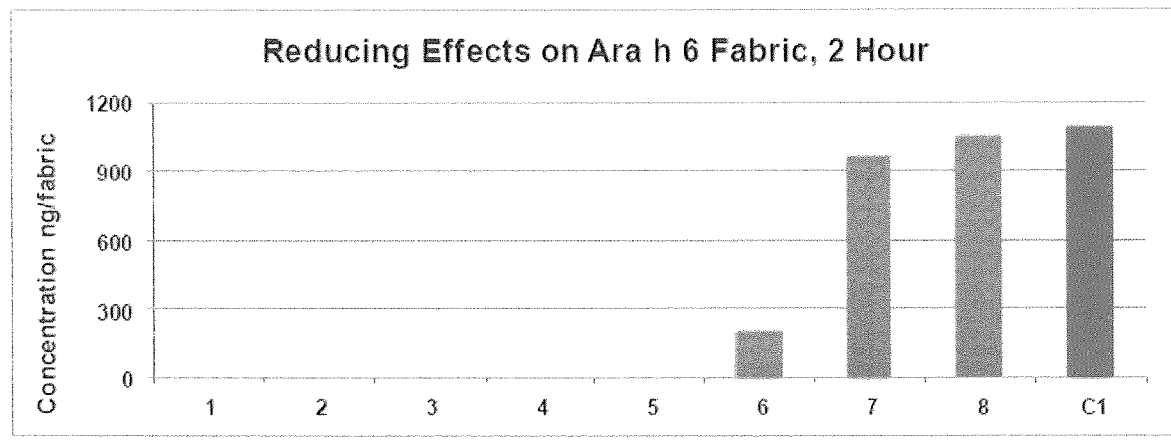
FIG. 28A is a graph showing the ability of a test formulation to deactivate Ara h6 on a fabric substrate 2 hours after application.
Figure 28B:
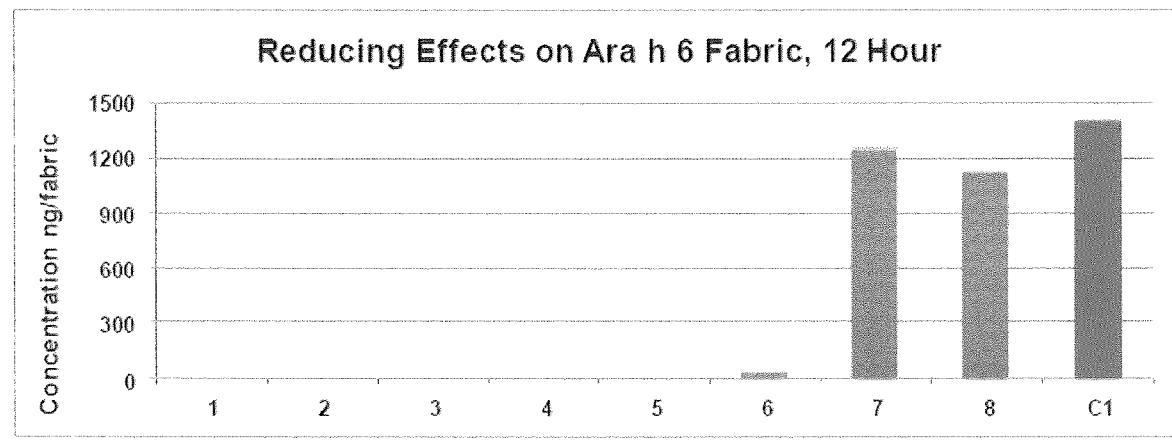
FIG. 28B is a graph showing the ability of a test formulation to deactivate Ara h6 on a fabric substrate 12 hours after application.

Levels of allergen activity were again determined via MARIA® allergen detection. Testing showed variations in the effect against certain allergens at different times based on the 2 hour and 12 hour data, which are illustrated FIG. 20a through FIG. 28b.

Hard Surface Testing

Hard surface studies were conducted by inoculating 35 mm diameter petri dishes with 0.5 mL of allergen concentrate. The dishes were then allowed to dry overnight. To each dish was then added 4.5 mL of test product (Formulas 9 through 15). After one minute, the dish was wiped with a clean wipe. Both dish and wipe were extracted to determine allergen activities.

All results generally showed that any product, including the water control, removed much of the allergen from the dish surface. However, the degree to which the product deactivated allergens (whether attached to the wipe or remaining on the dish surface) varied. Percent deactivation of the different allergens by the control (DI water) and Formulas 9 through 15 is shown in Table 6. As can be seen in the results, Formulas 9, 10, and 11 are the most effective in regards to percent deactivation.

TABLE 6

| | Percent Deactivation of Allergen (Wipe Plus Dish) | | | | | | | |
|---|---|---|---|---|---|---|---|---|
| Solution | Der p1 | Der f1 | Fel d1 | Can f1 | Bet v1 | Phl p5 | Mus m1 | Ara h6 |
| Control | 76 | 72 | 87 | 79 | 91 | 90 | 27 | 73 |
| 9 | 99 | 97 | 79 | 88 | 99 | 94 | 79 | 100 |
| 10 | 99 | 98 | 83 | 90 | 99 | 88 | 75 | 100 |
| 11 | 96 | 93 | 75 | 82 | 97 | 82 | 53 | 100 |
| 12 | 79 | 79 | 96 | 83 | 100 | 97 | 94 | 95 |
| 13 | 78 | 75 | 85 | 70 | 78 | 84 | 5 | 78 |
| 14 | 66 | 75 | 84 | 73 | 75 | 5 | 46 | 71 |
| 15 | 58 | 69 | 82 | 70 | 80 | 48 | 29 | 64 |

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms

The invention claimed is:

1. An anti-allergen com position consisting of:
   a peroxide in an amount of about 0.1 to about 12 wt. % based on the total weight of the anti-allergen composition;
   about 0.1 to about 0.5 wt. % of a pH adjusting agent selected from the group consisting of citric acid, malic acid, gluconic acid and combinations thereof;
   one or more optional surfactant;
   one or more optional fragrance; and
   water;
   wherein the anti-allergen composition has a pH of less than 5.

2. The anti-allergen composition of claim 1, wherein the peroxide is present in an amount of about 2 to about 6 wt. %.

3. The anti-allergen composition of claim 1, wherein the composition has a pH of about 2 to about 4.

4. The anti-allergen composition of claim 1, wherein the optional surfactant is present.

5. The anti-allergen composition of claim 4, wherein the surfactant is present in an amount of about 0.1 to about 3 wt. %.

6. The anti-allergen composition of claim 4, wherein the surfactant is an ethoxylated alcohol.

7. A method for deactivating allergens on a substrate, the method comprising applying to the substrate an anti-allergen composition according to claim 1 in an amount effective to deactivate at least a portion of the allergens present on the substrate.

8. The method of claim 7, wherein the substrate is a fibrous material.

9. The method of claim 8, wherein the fibrous material comprises one or more of upholstery, carpeting, draperies, or clothing.

10. The method of claim 7, wherein the substrate comprises one or more of wood, stone, ceramic, vinyl, or a laminate.

11. The method of claim 7, wherein the allergens comprise at least one of a dust mite allergen, a cat allergen, a dog allergen, a mouse allergen, a pollen allergen, a grass allergen, a mold allergen, or a nut allergen.

* * * * *